United States Patent [19]

Sommer

[11] Patent Number: 5,007,297

[45] Date of Patent: Apr. 16, 1991

[54] PARTICLE SIZE MEASURING SYSTEM WITH AUTOMATIC DILUTION OF SAMPLE

[75] Inventor: Holger T. Sommer, Greenbelt, Md.

[73] Assignee: Pacific Scientific Company, Newport Beach, Calif.

[21] Appl. No.: 280,334

[22] Filed: Dec. 6, 1988

[51] Int. Cl.$^5$ ............................................. G01N 15/00
[52] U.S. Cl. ................................................. 73/865.5
[58] Field of Search ............... 73/863, 863.01, 865.5, 73/865.8; 356/335, 336; 366/142, 273, 274; 324/71.4

[56] References Cited

U.S. PATENT DOCUMENTS

| | | | |
|---|---|---|---|
| 3,790,760 | 2/1974 | Stiller | 356/335 |
| 3,854,321 | 12/1974 | Dahneke | 73/865.5 |
| 4,199,265 | 4/1980 | Sanderson et al. | 366/274 |
| 4,227,815 | 10/1980 | Hoffa | 366/273 |
| 4,287,757 | 9/1981 | Bucsky et al. | 73/865.5 |
| 4,779,451 | 10/1988 | Ezawa et al. | 73/865.5 |
| 4,794,806 | 1/1989 | Nicoli et al. | 73/863.01 |
| 4,842,406 | 6/1989 | Von Bargen | 356/336 |

Primary Examiner—Robert Raevis
Attorney, Agent, or Firm—Lane, Aitken & McCann

[57] ABSTRACT

In a particle size measuring system with automatic dilution of the sample containing particles to be measured, the sample is diluted with ionized water in a mixing chamber while continuously withdrawing the mixture of the diluent and the sample in a stream from the mixing chamber. The size of the particles in the stream drawn from the mixing chamber are measured. To insure that the particle size distribution in the stream drawn to the mixing chamber is the same as that in the original sample, a stirrer is provided in the mixing chamber which repeatedly is reversed in its direction of rotation with the time intervals between successive reversals being randomly varied. A cleaning system is provided to clean the mixing chamber as well as the measuring cell in which particle sizes are measured.

6 Claims, 1 Drawing Sheet

PARTICLE SIZE MEASURING SYSTEM WITH AUTOMATIC DILUTION OF SAMPLE

This invention relates to an automatic dilution system for diluting a liquid sample in which it is desired to measure the relative particle sizes.

BACKGROUND OF THE INVENTION

Particle sizes and liquid samples can be measured by passing the liquid stream to be measured through a beam of light, preferably a laser beam, and measuring the characteristics of the light scattered from the sample or the unscattered portion of the beam through which the sample has passed. U.S. patent application Ser. No. 144,225, filed Jan. 15, 1988 and invented by Kenneth Paul Von Bargen discloses such a system for measuring particle sizes in liquid streams. The system of the above mentioned patent application and most other prior art systems for measuring particle size require that a small number of particles, e.g., one at a time, pass through the laser beam. Thus, when the particle density in the sample is too great, there is a need to dilute the sample before making the particle size measurements.

In particle size measuring applications, there is a need to know the relative numbers of particles in different size ranges. The absolute numbers of the particles in each size range in the sample in many applications is not important. An automatic dilution system has been proposed to take advantage of this latter fact. This system automatically dilutes the sample by continuously introducing diluent into a mixing chamber containing the sample to be measured while the mixture of the diluent and sample in the mixing chamber is allowed to continuously flow from the mixing chamber. With such an arrangement, the mixture in the mixing chamber will continuously become more diluted. When the mixture has become sufficiently diluted, the particle size measurements are made. With this technique, the degree of dilution of the original sample is not known, but, theoretically, the relative counts of particles in each size range will give an accurate indication of the relative number of particles in each size range in the original sample.

As a practical matter, the automatic dilution system of the above described proposal may not give an accurate count of particles in each size range, because in this system the mixing carried out in the mixing chamber was simply that which occurred as a result of the diluent stream flowing into the mixing chamber. The inflow of the diluent result in a whirlpool flow pattern which tends to cause the particles of different sizes to segregate. As a result, the outflow from the mixing chamber may fail to contain a distribution of particle sizes corresponding to their distribution in the original sample, and the system of the proposal may fail to give accurate counts of the relative particle sizes.

SUMMARY OF THE PRESENT INVENTION

The present invention improves over the system of the proposal by providing a mixing mechanism and method in the mixing chamber which assures that turbulent mixing devoid of any pattern occurs throughout the mixing chamber and, thus, ensures that the particle sizes are uniformly distributed in the chamber and in the diluted sample exiting from the mixing chamber. This mixing method involves introducing the diluent into the mixing chamber from an inlet conduit which directs the diluent tangentially along the cylindrical vertical wall of the mixing chamber. In addition, a stirrer is provided at the bottom of the mixing chamber and is caused to rotate, for part of the time, in the opposite direction to the tangential flow of the diluent being introduced into the chamber. This stirring in the opposite direction to the direction in which the diluent is introduced into the chamber causes turbulent mixing to occur throughout the mixing chamber. The direction of rotation of the stirrer is repeatedly reversed with the time period between reversals randomly changing so that no pattern develops in the turbulent flow in the mixing chamber.

In addition, the present invention comprises an improved system for cleaning and maintaining clean the mixing chamber between measurements of successive samples and also for reducing the contamination of the measuring cell by the mixture when it is still relatively concentrated. In accordance with this improved system, while the sample is initially being diluted and while it is still highly concentrated, the outflow from the mixing chamber is bypassed around the measuring cell so that it is not contaminated by outflow from the mixing chamber. When the sample becomes sufficiently diluted, the outflow from the measuring cell is allowed to flow through the measuring cell so that the measuring cell may be used in determining when the sample is sufficiently diluted to make a measurement. Before a new sample is introduced, the mixing chamber may be automatically cleaned. In the cleaning process, the mixing chamber may be first flushed with tap water bypassing the measuring cell. Following flushing with tap water, the mixing chamber is then flushed with the diluent, which is deionized water, while still bypassing the measuring cell. Finally, the mixing chamber and the measuring cell are flushed with the deionized water to provide a thorough cleaning of both the mixing chamber and the measuring cell while reducing the chances of the measuring cell becoming contaminated with remnants from the previous sample.

DESCRIPTION OF A PREFERRED EMBODIMENT

Figure 1:
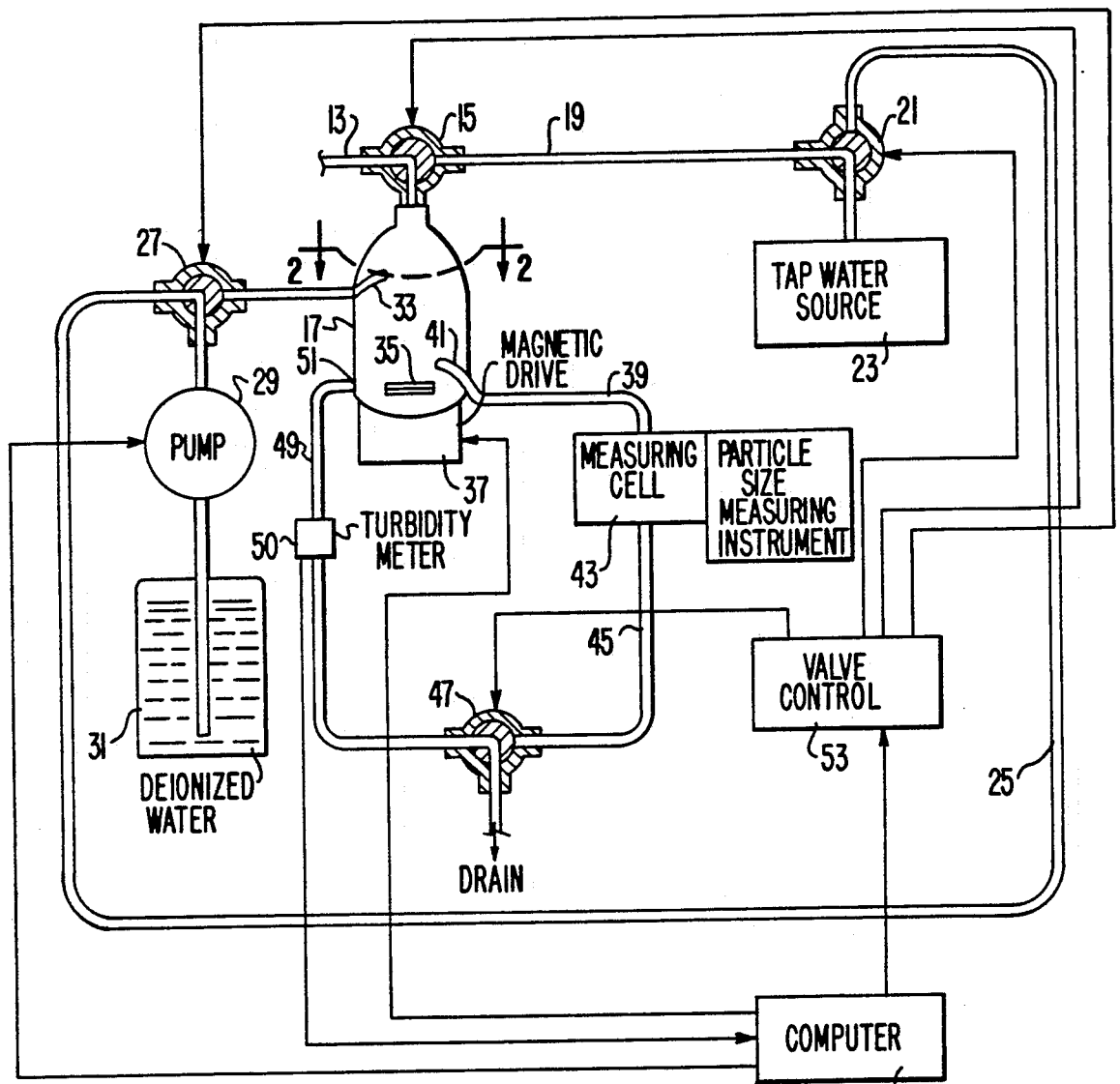
FIG. 1 is a schematic diagram illustrating the system of the invention.
Figure 2:
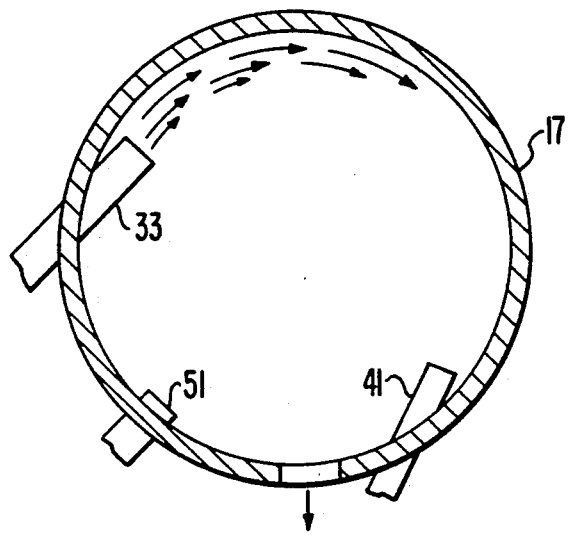
FIG. 2 is a sectional view taken along the lines 2—2 of the mixing chamber shown in FIG. 1 illustrating the details of the mixing chamber.

As shown in FIG. 1, the sample containing the particle sizes to be measured is introduced into a mixing chamber 17 through a valve 15 controlling inflow into the top of the mixing chamber 17. The sample may be introduced from a syringe, not shown. In one position, the valve 15 opens to an inlet 13 to receive the sample from the syringe and direct the sample in to the mixing chamber 17 and in the other position, it will open the top of the mixing chamber 17 to a conduit 19. The conduit 19 leads to a valve 21, which is also connected to a source of tap water 23 and to a conduit 25. In one position, the valve 21 connects the source of tap water to the conduit 19, and in its other position, the valve 21 connects the conduit 25 to the conduit 19. The conduit 25 leads to a valve 27 which is also connected through a pump 29 to a tank 31 containing the deionized water. The valve 27 is also connected to an inlet nozzle 33 extending through the wall of the mixing chamber 17. In one position, the valve 27 will connect the pump 29 to the conduit 25 and in a second position, will connect the pump 29 to the nozzle 33. The mixing chamber 17 has a cylindrical side wall and, as better shown in FIG. 2, the nozzle 33 is pointed to direct a stream tangential to the cylindrical side wall. The nozzle 33 as best shown in FIG. 1 is positioned near the top of the cylindrical portion of the mixing chamber 17. In the bottom of the mixing chamber 17 is an elongate stirring element 35, which rests on the bottom of the mixing chamber 17 and is magnetically driven by a magnetic drive unit 37. When the element is being driven by the magnetic drive unit, its long dimension will lie along a diameter of the bottom of the mixing chamber and it will be rotated about the axis of the mixing chamber 17. The inlet end 41 of a conduit 39 extends through the wall of the mixing chamber 17 near the bottom thereof and has its axis pointed tangentially along the cylindrical wall of the mixing chamber 17 in the opposite direction to the direction in which the nozzle 33 is pointed. The conduit 41 leads to the measuring cell 43 of a particle size measuring instrument 44 such as disclosed in the Von Bargen copending application Ser. No. 144,225 mentioned above. As disclosed in this application, the particle size measuring instrument will count the number of particles in a liquid sample passing through the measuring cell in each of a plurality of narrow size ranges extending over a wide total size range. The outlet side of the measuring cell 43 is connected through a conduit 45 to a valve 47, which is also connected to a drain. A second outlet 51 in the bottom of the mixing chamber 17 is connected through a conduit 49 and a turbidity meter 50 to the valve 47. In one position, the valve 47 will connect the turbidity meter 50 to the drain and in the other position, the valve 47 will connect the conduit 45 leading from the outlet of the measuring cell 43 to the drain.

Each of the valves 15, 27, 21 and 47 are controlled by a valve control unit 53 which in turn is controlled by a computer 55. The computer 55 also controls the operation of the pump 33 and the magnetic drive unit 37. The system as shown in FIG. 1 has six different modes of operation to perform the various functions of the system including introducing the sample, flushing the system with tap water, flushing the mixing chamber with deionized water while bypassing the sensor, flushing the mixing chamber and the measuring cell with deionized water, introducing diluent into the mixing chamber while bypassing the measuring cell, and introducing diluent into the mixing chamber while the mixed effluent from the mixing chamber is caused to flow through the measuring cell 43.

When the sample is introduced into the chamber 17, the valve control unit 53 under the control of the computer 55 will actuate the valve 15 to open the inlet 13 into the mixing chamber 17 to allow the sample to flow into the mixing chamber 17. At the same time, the valve control unit 53 will actuate the valve 21 to connect the conduit 19 to the conduit 25 so that the source of tap water 23 is disconnected from the system. The valve 27 will be actuated to connect the pump 29 to the conduit 25 so that it is disconnected from the nozzle 33. The valve 47 will connect the outlet 51 to the drain so that the measuring cell 43 is disconnected from the drain, and so that there will be no flow of the sample into the measuring cell while the sample is being introduced into the mixing chamber. While the sample is being introduced, the computer 55 will de-energize the pump 29 and the magnetic drive unit 37. Following introduction of the sample, the computer will control the valve control unit 53 and the pump 29 to enter the mode to dilute the sample while bypassing the measuring cell. In this mode, the pump 29 is turned on, the valve 27 is moved to a position in which the pump 29 is connected to the nozzle 33 to cause the diluent, deionized water, to flow into the mixing chamber. The valve 15 will be switched to disconnect the inlet 13 from the mixing chamber 17 and, instead, the valve 15 will connect the top of the mixing chamber to a conduit 19. The valve 21 will be maintained in the position in which it connects the conduit 19 to the conduit 25, which at its other end, is disconnected by the position of the valve 27. The valve 47 in this mode will be positioned to connect the turbidity meter 50 to the drain so that effluent from the mixing cell flows out the through the conduit 49 and the turbidity meter 50 to the drain while bypassing the measuring cell. During this mode of operation, the computer will also actuate the magnetic drive unit 37 to stir the mixture in the mixing chamber 17 while repeatedly reversing direction. In this operation, the computer changes the duration of each interval between reversals of the stirrer to vary randomly between ½ second and 10 seconds. This variation is achieved by programming the computer to generate random numbers and setting each interval to correspond to a randomly generated number. While the sample is being diluted in this mode, the computer 55 monitors the output signal of the turbidity meter indicating the turbidity of the outflow from the mixing chamber. When the computer detects that the turbidity of the sample is sufficiently low indicating that the sample in the mixing chamber has become sufficiently diluted to make particle size measurements, the computer 55 will signal the valve control unit 53 to switch to the measuring mode in which the sample is diluted while passing the effluent from the mixing chamber through the measuring cell 43. In this mode, the valves 15, 27, 21 are kept in their same positions and the valve 47 is switched to connect the drain to the conduit 45 connected to the outlet side of the measuring cell 43. The computer 55 continues the activation of the pump 29 as well as the magnetic drive 37. As a result, the diluent will continue to be introduced into the mixing chamber 17 through the nozzle 33, but the effluent from the mixing chamber 17 will flow through the measuring cell 43 to the drain. In this mode, the computer 55 will continue to repeatedly reverse the direction that the stirrer is being driven with time intervals between each reversal varying randomly between one-half second and 10 seconds. When the computer 55 switches to the measuring mode, the effluent from the mixing chamber should be sufficiently dilute so that particles are passing through the laser beam of the measuring cell one at a time. If so, the particle size measuring instrument 44 will count the particles in each size range over a time interval sufficient to obtain a statistically significant count in each size range. If the effluent is not sufficiently dilute for one particle at a time to pass through the laser beam of the measuring cell, the output signal from the measuring cell, instead of being a pulse train of narrow width pulses, will be a constant high level signal or be a series of wider pulses. Circuitry is provided in the measuring instrument 44 to recognize this characteristic of the output signal of the measuring cell, and the measuring instrument will not begin counting particle sizes until the measuring cell output comprises a train of pulses of the proper width. While the sample is being diluted and while the particle sizes are being counted, a high degree of turbulence in the mixing chamber is assured by having the stirrer 35 rotate at least part of the time in a direction opposite to the direction that the deionized water is introduced through the nozzle 33. The turbulence is further increased by repeatedly reversing the direction of the stirrer 35 during the dilution of the sample. Because the time interval between reversals is randomly varied, the turbulent flow is not in any pattern. As a result, the particle sizes are randomly distributed in the mixing chamber and occur in the effluent from the mixing chamber with the same frequency relative to each other that they do in the original sample.

Following the counts of the particle sizes in the different size ranges, the computer 55 continues the introduction of the diluent while causing outflow through the measuring cell for a time interval sufficient to clean the mixing chamber and the measuring cell.

Before introducing the sample into the measuring cell, the computer 55 can be controlled to carry out a cleaning cycle, in which the mixing chamber is first flushed with tap water and then with deionized water. During this cleaning cycle, the computer actuates the magnetic drive unit to stir the contents of the mixing chamber. In the first part of the cleaning cycle, the valve control unit 53 switches the valve 21 to connect the tap water source 23 to the conduit 19. The valve 15 is positioned to connect the top of the mixing chamber 17 to the conduit 19 so that tap water flows into the mixing chamber 17. The valve control unit will switch the valve 47 to the position to connect the outlet 51 and the conduit 49 to the drain so that the tap water after flushing the mixing chamber 17 will flow out through the conduit 49 to the drain while bypassing the measuring cell 43. The valve 27 will be switched to a position in which it disconnects from the nozzle 33 and connects the conduit 25 to the pump 29.

Following the flushing of the mixing chamber 17 for a predetermined period of time with tap water, the computer will signal the valve control unit 53 to switch to the mode of flushing with deionized water while bypassing the sensor. On this mode, the valve 15 will remain in its position connecting the conduit 19 to the top of the mixing chamber 17. The valve 21 will switch to connect the conduit 19 to the conduit 25. The valve 27 will remain in the position to connect the conduit 25 to the pump 29, which, in this mode, will be activated so that deionized water is pumped from the tank 31 through the conduit 25 and the conduit 19 into the top of the mixing chamber 17. The valve 47 will remain in its position to connect the conduit 49 to the drain sb that the deionized water flushes the mixing chamber 17 while bypassing the sensor 43.

Following the flushing of the mixing chamber 17 with the deionized water while bypassing the measuring cell 43 for a predetermined period of time, the computer 51 will signal the valve control 53 to switch to the mode of flushing the mixing chamber 17 and the measuring cell 43. To switch to this mode of operation, the valve 47 is switched to connect the drain to the conduit 45 with the other valves remaining in their position and with the pump 29 remaining activated so that the deionized water entering the mixing chamber 17 through the valve 15 will be diverted through the measuring cell.

In many applications, flushing with tap water is not necessary and this part of the cleaning cycle can be eliminated both as a step and in the plumbing connections to carry out this step. Also, when several samples are to be counted in succession, the cleaning that is achieved after the measurement has been completed by continuing to introduce diluent into the mixing chamber after the end of the interval, may be sufficient that no additional cleaning is required and the cleaning cycle described above may be omitted entirely before each succeeding sample is introduced.

As described above, the direction that the stirrer is driven is repeatedly reversed and the time interval randomly varied. The repeated reversals add to the turbulence and the random time intervals insures that there is no pattern in the turbulent flow that might tend to separate particles by particle size. However, a high degree of turbulence is achieved simply by having the stirrer rotate in the opposite direction from the direction that the diluent is introduced into the mixing chamber and improved count accuracy is achieved simply by employing this feature without repeatedly reversing the direction of the stirrer.

These and other modifications may be made to the above described specific embodiment of the invention without departing from the spirit and scope of the invention, which is defined in the appended claims.

I claim:

1. A particle measuring system comprising a mixing chamber for receiving a sample of particles to be measured, means to continuously introduce a diluent into said mixing chamber while withdrawing a mixture of said diluent and said sample from said mixing chamber, measuring means to receive a mixture of said diluent and said sample from said mixing chamber in a fluid stream and to measure the size of the particles entrained in said fluid stream, a stirrer within said mixing chamber, and control means to rotate said stirrer within said mixing chamber while automatically repeatedly reversing the direction of rotation of said stirrer, wherein said control means reverses the direction of rotation of said stirrer after an interval which varies randomly between limits.

2. A particle measuring system comprising a mixing chamber for receiving a sample containing particles to be measured, means to continuously introduce a diluent into said mixing chamber, a measuring cell, means to measure the size of particles passing through said cell in a fluid stream, bypass means to withdraw a mixture of said diluent and said sample from said mixing chamber while said diluent is being introduced continuously into said chamber bypassing said measuring cell, measuring cell connecting means for withdrawing a mixture of said diluent and said sample from said mixing chamber in said fluid stream directed through said measuring cell, and means responsive to the turbidity of the mixture withdrawn by said bypass means to deactivate said bypass means and activate said measuring cell connecting means to begin the fluid flow through said measuring cell when the turbidity of the mixture being withdrawn by said bypass means drops below a predetermined value.

3. A particle size measuring system comprising a mixing chamber for receiving a sample of particles to be measured, means including an inlet conduit to continuously introduce a diluent into said mixing chamber through said inlet conduit having a diameter while withdrawing a mixture of said diluent and said sample from said mixing chamber, said mixing chamber having a height substantially greater than the diameter of said inlet conduit and having a horizontal sectional area substantially larger than the cross sectional area of said inlet conduit throughout the height of said mixing chamber, measuring means to receive said mixture of said diluent and said sample from said mixing chamber in a fluid stream and measure the size of particles entrained in said fluid stream, and cleaning means to direct a flow of cleaning fluid through said mixing chamber bypassing said measuring means prior to introducing said sample into said mixing chamber.

4. A particle measuring system as recited in claim 3 wherein said means to measure the size of particles in said fluid stream comprises a measuring cell to receive said fluid stream and wherein said cleaning means is operable to flush said measuring cell with said cleaning fluid.

5. A particle measuring system as recited in claim 3, wherein said cleaning means includes valve means operable to automatically first withdraw said cleaning fluid from said mixing chamber bypassing said measuring cell and then to withdraw said cleaning fluid from said mixing chamber through said measuring cell to flush said measuring cell with said cleaning fluid.

6. A method of measuring particle sizes in a concentrated sample comprising the steps of introducing a sample of particles to be measured into a mixing chamber, continuously introducing a diluent into said mixing chamber while withdrawing a mixture of said sample and said diluent from said chamber in a fluid stream, rotating a stirrer in said mixing chamber while repeatedly reversing the direction of said stirrer to introduce turbulence into said mixing chamber while said mixture of said sample and said diluent is being withdrawn from said mixing chamber in said fluid stream, randomly varying the interval between each successive reversal of rotation of said stirrer, and measuring the size of the particles in said fluid stream.

* * * * *